United States Patent [19]
Takaya et al.

[11] 4,016,160
[45] Apr. 5, 1977

[54] 7-DIHALOALKANAMIDO-3-HETEROCYCLIC-THIOMETHYL-3-CEPHEM-4-CARBOXYLIC ACIDS

[75] Inventors: Takao Takaya, Sakai; Takashi Masugi, Toyonaka, both of Japan

[73] Assignee: Fujisawa Pharmaceutical Co., Ltd., Osaka, Japan

[22] Filed: June 18, 1975

[21] Appl. No.: 587,854

[52] U.S. Cl. .............................. 260/243 C; 424/246
[51] Int. Cl.² ........................................ C07D 501/20
[58] Field of Search ................................ 260/243 C

[56] References Cited
UNITED STATES PATENTS 3,555,017 1/1971 Bickel et al. ................... 260/243 C
3,855,213 12/1974 Dunn et al. ..................... 260/243 C

*Primary Examiner*—Nicholas S. Rizzo
*Attorney, Agent, or Firm*—Dayton R. Stemple, Jr.

[57] ABSTRACT

The present invention relates to new cephalosporanic acids and their derivatives and preparation thereof. More particularly, it relates to 7-dihaloalkanoylamido-3-heterocyclic-thiomethyl-3-cephem-4-carboxylic acids, their derivatives and their nontoxic pharmaceutically acceptable salts, which possess an antibacterial activity, process for preparation of the same and compositions thereof.

10 Claims, No Drawings

7-DIHALOALKANAMIDO-3-HETEROCYCLIC-THIOMETHYL-3-CEPHEM-4-CARBOXYLIC ACIDS

INVENTION

The objective cephalosporanic acids and derivatives of the present invention include compounds represented by the following general formula:

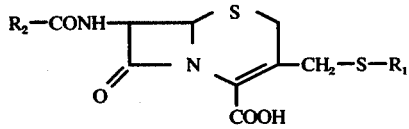 [I]

wherein $R_1$ is heterocyclic group which may be substituted with lower alkyl groups(s), and $R_2$ is dihalo(lower)alkyl group, their derivatives at the carboxy group and their nontoxic pharmaceutically acceptable salts.

The term "lower" used in this specification and the claims is intended to mean radical containing 1 to 6 carbon atom(s).

The term "heterocyclic group" may be 5 to 6 membered heterocyclic group containing nitrogen atom(s), nitrogen and sulfur atoms or nitrogen and oxygen atoms which, for example, includes a residue of pyrrole, pyrazole, imidazole, triazole, tetrazole, pyridine, pyrazine, pyrimidine, pyridazine, pyrroline, pyrrolidine, imidazoline, imidazolidine, piperidine, tetrahydropyrimidine, hexahydropyrimidine, hexahydropyridazine, thiazole, thiazoline, isothiazole, thiadiazole, oxazole, oxazoline, isoxazole or oxadiazole, benzene-fused 9 to 10 membered heterocyclic group containing nitrogen atom(s), nitrogen and sulfur atoms or nitrogen and oxygen atoms which, for example, includes a residue of indole, indoline, indazole, benzimidazole, quinoline, isoquinoline, dihydroisoquinoline, tetrahydroisoquinoline, phthalazine, quinoxaline, quinazoline, purine, naphthyridine, benzothiazole, benzothiadiazole, benzoxazole or benzoxadiazole or the like.

These heterocyclic groups may be substituted with one or more lower alkyl or cycloalkyl groups such as methyl, ethyl, propyl, isopropyl, butyl, isobutyl, tert-butyl, pentyl, hexyl, cyclopentyl, cyclohexyl, or the like.

The term "dihalo(lower)alkyl group" may be a lower alkyl group substituted with two halogen atoms such as difluoromethyl, dichloromethyl, dibromomethyl, diiodomethyl, 1,2-difluoroethyl, 1,2-dichloroethyl, 1,2-dibromoethyl, 1,2-diiodoethyl, 2,2-difluoroethyl, 2,2-dichloroethyl, 2,2-dibromoethyl, 2,2-diiodoethyl, 3,3-difluoropropyl, 3,3-dichloropropyl, 3,3-dibromopropyl, 3,3-diiodopropyl, bis(chloromethyl)methyl, 4,4-difluorobutyl, 4,4-dichlorobutyl, 4,4-dibromobutyl, 4,4-diiodobutyl, 5,5-difluoropentyl, 5,5-dichloropentyl, 5,5-dibromopentyl, 5,5-diiodopentyl, 6,6-difluorohexyl, 6,6-dichlorohexyl, 6,6-dibromohexyl, 6,6-diiodohexyl, or the like.

The term "derivative at the carboxy group" of the compound [I] may be an ester such as lower alkyl ester (e.g., methyl ester, ethyl ester, propyl ester, isopropyl ester, butyl ester, isobutyl ester, pentyl ester, hexyl ester or 1-cyclopropylethyl ester), lower alkenyl ester (e.g., allyl ester or vinyl ester), alkynyl ester (e.g., ethynyl ester or propynyl ester), halo(lower)-alkyl ester (e.g., 2-iodoethyl ester or 2,2,2-trichloroethyl ester), lower alkanoyloxy(lower)alkyl ester (e.g., acetoxymethyl ester, propionyloxymethyl ester, butyryloxymethyl ester, valeryloxymethyl ester, pivaloyloxymethyl ester, 2-acetoxyethyl ester or 2-propionyloxyethyl ester), 2-mesylethyl ester, phenyl(lower)alkyl ester in which the phenyl moiety may have suitable substituent(s), (e.g., benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester or 4-hydroxy-3,5-di-tert-butylbenzyl ester), aryl ester (e.g., phenyl ester, tolyl ester, xylyl ester, mesityl ester or cumenyl ester), or the like.

The term "nontoxic pharmaceutically acceptable salt" may be a salt such as alkali metal salt (e.g., sodium salt or potassium salt), organic amine salt (e.g., triethylamine salt, dicyclohexylamine salt, diphenylenediamine salt, dibenzylethylenediamine salt, ethanolamine salt, diethanolamine salt, pyrrolidine salt, N-methylpiperidine salt or piperazine salt), or the like.

The objective 7-dihalo(lower)alkanamido-3-heterocyclicthiomethyl-3-cephem-4-carboxylic acids [I] and their derivatives and salts may be prepared by reacting 7-amino-3-heterocyclic-thiomethyl-3-cephem-4-carboxylic acid of the general formula:

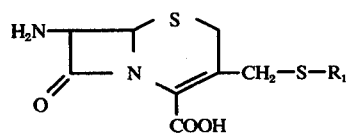 [II]

wherein $R_1$ is as defined above, or its derivative at the amino and/or carboxy group or a salt thereof, with dihalo(lower)alkanoic acid of the general formula:

  $R_2$—COOH [III]

wherein $R_2$ is as defined above, or its reactive derivative at the carboxy group or a salt thereof.

The derivative at the amino group of the compound [II] may be an acid addition salt, Schiff's base or its tautomeric enamine type isomer or a silyl derivative formed by the reaction of the compound [II] with a silyl compound such as bis(trimethylsilyl) acetamide, or the like.

The derivative at the carboxy group of the compound [II] is the same as the one of the compound [I] as mentioned above.

The reactive derivative at the carboxy group of the compound [III] may be an acid halide, an acid anhydride, an activated amide, an activated ester, or the like. The suitable examples may be an acid chloride; an acid azide; a mixed acid andydride with an acid such as dialkylphosphoric acid, phenylphosphoric acid, diphenylphosphoric acid, dibenzylphosphoric acid, halogenated phosphoric acid, dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid or trichloroacetic acid) or aromatic carboxylic acid (e.g. benzoic acid) or a symmetrical acid anhydride; an activated amide of imidazole, 4-substituted imidazole, dimethylpyrazole, triazole or tetrazole; or an activated ester (e.g. cyanomethyl ester, methoxymethyl ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester; or an ester of N,N-dimethylhydroxylamine, 1-dihydroxy-2-(1H)-pyridone, N-hydroxysuccinimide, N-hydroxyphthalimide or 1-hydroxy-6-chloro1H-benzotriazole), or the like. The suitable derivative can be optionally selected from them according to the kind of the compound [III] to be used.

The reaction is usually carried out in a solvent such as water, acetone, dioxane, acetonitrile, chloroform, methylene chloride, ethylene chloride, tetrahydrofuran, ethyl acetate, N,N-dimethyl formamide, pyridine or any other organic solvent inert to the reaction. Among these solvents, hydrophilic solvents may be used in a mixture with water.

When the free acid or the salt of the compound [III] is used in the reaction, the reaction is preferably carried out in the presence of a condensing agent such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonylbis(2-methylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, 2-ethyl-7-hydroxybenzisoxazolim salt, 2-ethyl-5-(m-sulfophenyl)isoxazolium hydroxide intramolecular salt, (chloromethylene)dimethylammonium chloride, or the like. The salt of the compound [III] may be an alkali metal salt, an alkaline earth metal salt, an ammonium salt, a salt with an organic base such as triethylamine, dicyclohexylamine, or the like.

The reaction may be also carried out in the presence of an inorganic or an organic base such as alkali metal bicarbonate, trialkylamine, pyridine, N-alkylmorpholine, N,N-dialkylbenzylamine, or the like. A liquid base or condensing agent may be used as a solvent. The reaction temperature is not restrictive, and the reaction is usually carried out under cooling or at ambient temperature.

The reaction using a derivative at the carboxy group of the compound [II] or a salt thereof as the starting material may give occasionally an objective compound [I] in a form of the free acid, and these cases are also included in the scope of the present invention.

When the compound [I] thus obtained is a free acid, it may be converted into its salt such as alkali metal salt (e.g., sodium salt or potassium salt), organic amine salt (e.g., triethylamine salt, dicyclohexylamine salt), or the like by a conventional method.

In accordance with the present invention, precipitates which form by the reaction is separated from the reaction mixture by methods commonly used for this purpose, and the resultant reaction product may be subjected to purification procedures, for instance, to recrystallization from an appropriate solvent or a mixture of such solvents.

The compounds [I] of the present invention and their derivatives and salts thereof exhibit a high antibacterial activity. For therapeutic administration the cephalosporin compounds according to the present invention are used in the form of pharmaceutical preparations which contain said compounds in admixture with a pharmaceutically acceptable organic or inorganic solid or liquid excipient suitable for parenteral administration. The pharmaceutical preparations may be in dragees, or in liquid form such as solutions, suspensions, or emulsions, or suppository. If desired, there may be included in the above preparations auxiliary substances, stabilizing agents, wetting or emulsifying agents, buffers and other commonly used additives.

The effective dosage of the compound [I] according to the present invention will depend upon the age and condition of the patient suffered from bacterial infection and vary, for instance, 10 mg., 50 mg., 100 mg., 250 mg., 500 mg., and 1000 mg.

The following examples are given for the purpose of illustrating the present invention.

EXAMPLE 1

7-Amino-3-(1,3,4-thiadiazol-2-ylthiomethyl)-3-cephem-4-carboxylic acid (6.61 g) was suspended in methylene chloride (60 ml) and bis(trimethylsilyl)acetamide was added to the suspension to give a solution. A solution of dichloroacetyl chloride (3.24 g) in methylene chloride (10 ml) was added to the solution obtained above at −20° C under stirring. The mixture was stirred at the same temperature for 20 minutes. Methylene chloride was distilled off under reduced pressure after addition of a little water. Water was added to the residue and the mixture was extracted with ethyl acetate. The extract was washed with saturated aqueous sodium chloride and dried, and the solvent was distilled off under reduced pressure. The residue was pulverized by treating with ether and precipitates were collected by filtration to give 7-dichloroacetamido-3-(1,3,4-thiadiazol-2-ylthiomethyl)-3-cephem-4-carboxylic acid (7.12 g).

I.R.
$\nu_{max}^{Nujol}$ cm$^{-1}$ : 3250, 1770, 1690, 1660
N.M.R.
$\delta$(Dimethylsulfoxide-d$_6$)ppm :
9.72 (1H, d, J=9Hz)
9.6 (1H, s)
6.52 (1H, s)
5.7 (1H, d, d, J=5Hz, 9Hz)
5.2 (1H, d, J=5Hz)
4.5 (2H, q, J=13Hz)
3.78 (2H, q, J=18Hz)

EXAMPLE 2

7-Amino-3-(4H-1,2,4-triazol-3-ylthiomethyl)-3-cephem-4-carboxylic acid (3.13 g) was suspended in dried methylene chloride (30 ml) and bis(trimethylsilyl)acetamide (6.10 g) was added to the suspension to give a solution. A solution of dichloroacetyl chloride (1.62 g) in dried methylene chloride (20 ml) was added slowly to the solution at −20° C. The mixture was stirred at the same temperature for 30 minutes and then allowed to stand at room temperature. Methylene chloride was distilled off from the reaction mixture under reduced pressure. To the residue was added ice water and the aqueous solution was adjusted to pH 8 with 5% aqueous sodium bicarbonate, washed with ethyl acetate and then filtered. The filtrate was adjusted to pH 2 with 10% hydrochloric acid and extracted with ethyl acetate (50 ml) three times. These extracts were put together, washed with water twice and with saturated aqueous sodium chloride and dried over magnesium sulfate. Ethyl acetate was distilled off from the solution under reduced pressure. To the residue was added ether and the mixture was stirred. Precipitates were collected by filtration and dried to give 7-dichloroacetamido-3-(4H-1,2,4-triazol-3-ylthiomethyl)-3-cephem-4-carboxylic acid (2.95 g).

I.R.
$\nu_{max}^{Nujol}$ cm$^{-1}$ : 3250, 1765, 1700, 1690
N.M.R.
δ(Dimethylsulfoxide-d$_6$)ppm:
9.60 (1H, d, J=10Hz)
8.42 (1H, s)
6.47 (1H, s)
5.70 (1H, d, d, J=6Hz, 10Hz)
5.13 (1H, d, J=6Hz)
4.18 (2H, d, d, J=13Hz)
3.68 (2H, d, d, J=18Hz)

EXAMPLE 3

7-Amino-3-(1-methyl-1H-tetrazol-5-ylthiomethyl)-3-cephem-4-carboxylic acid (3.28 g) was suspended in a mixture (60 ml) of water and acetone (1:1) and sodium bicarbonate was added to the suspension little by little to give a solution. Dichloroacetyl chloride (3 g) was added dropwise to the solution at −5° C under stirring and the mixture was stirred at the same temperature for 30 minutes. Ethyl acetate (50 ml) was added to the reaction mixture and the mixture was adjusted to pH 2 with diluted hydrochloric acid under stirring and filtered. The ethyl acetate layer was separated from the filtrate, washed with saturated aqueous sodium chloride, dried over magnesium sulfate and then treated with activated charcoal powder. Ethyl acetate was distilled off from the solution under reduced pressure. Ether was added to the residue and the mixture was stirred overnight. Precipitates were collected by filtration to give pale yellow powder of 7-dichloroacetamido-3-(1-methyl-1H-tetrazol-5-ylthiomethyl)-3-cephem-4-carboxylic acid (1.5 g).

I.R.
$\nu_{max}^{Nujol}$ cm$^{-1}$ : 3250, 1775, 1700, 1680
N.M.R.
δ(Dimethylsulfoxide-d$_6$)ppm:
9.7 (1H, d, J=9Hz)
6.52(1H, s)
5.70(1H, d, d, J=5Hz, 9Hz)
5.18(1H, d, J=5Hz)
4.35(2H, ABq, J=13Hz)
3.95(3H, s)
3.75(2H, ABq, J=18Hz)

EXAMPLE 4

7-Amino-3-(5-methyl-1,3,4-thiadiazol-2-ylthiomethyl)-3-cephem-4-carboxylic acid (6.89 g) was suspended in methylene chloride (60 ml) and bis(trimethylsilyl)acetamide (8.12 g) was added to the suspension to give a solution. A solution of dichloroacetyl chloride (3.24 g) in methylene chloride (10 ml) was added to the solution obtained above at −20° C under stirring. The mixture was stirred at the same temperature for 20 minutes and methylene chloride was distilled off from the mixture after addition of a little water. Water was added to the residue and the mixture was extracted with ethyl acetate. The extract was washed with saturated aqueous sodium chloride and dried. The solvent was distilled off from the solution under reduced pressure. The residue was pulverized by treating with ether and precipitates were collected by filtration and dried to give 7-dichloroacetamido-3-(5-methyl-1,3,4-thiadiazol-2-ylthiomethyl)-3-cephem-4-carboxylic acid (6.0 g).

I.R.
$\nu_{max}^{Nujol}$ cm$^{-1}$ : 3250, 1770, 1700, 1670
N.M.R.
δ(Dimethylsulfoxide-d$_6$)ppm:
9.7 (1H, d, J=9Hz)
6.53 (1H, s)
5.7 (1H, d, d, J=5Hz, 9Hz)
5.2 (1H, d, J=5Hz)
4.4 (2H, q, J=13Hz)
3.75 (2H, q, J=18Hz)
2.7 (3H, s)

EXAMPLE 5

7-Amino-3-(1H-1,2,3-triazol-5-ylthiomethyl)-3-cephem-4-carboxylic acid (0.98 g) was suspended in methylene chloride (10 ml) and bis(trimethylsilyl)acetamide (2.53 g) was added to the suspension to give a solution. To the solution was added dropwise a solution of dichloroacetyl chloride (0.46 g) in methylene chloride (10 ml) at −30° C. The mixture was stirred at −10°0 to −15° C for 30 minutes and then concentrated under reduced pressure. To the residue was added ethyl acetate (50 ml) and water (30 ml) and the mixture was stirred and filtered. The ethyl acetate layer was separated from the filtrate and concentrated under reduced pressure to a half of volume. Water (30 ml) was added to the concentrated solution and the mixture was adjusted to pH 7.2 by adding aqueous sodium bicarbonate under cooling and stirring. The aqueous layer was separated from the mixture, adjusted to pH 6 with diluted hydrochloric acid, washed with ethyl acetate, adjusted to pH 2 with diluted hydrochloric acid and then extracted with ethyl acetate. The extract was washed with saturated aqueous sodium chloride, dried over magnesium sulfate and treated with activated charcoal powder. Ethyl acetate was distilled off from the solution under reduced pressure. The residue was pulverized by treating with ether and precipitates were collected by filtration to give 7-dichloroacetamido-3-(1H-1,2,3-triazol-5-ylthiomethyl)-3-cephem-4-carboxylic acid (0.56 g). The solvent was distilled off from the mother liquid under reduced pressure and the residue was pulverized by treating with diisopropyl ether. Precipitates were collected by filtration to give the same product (0.14 g). Total yield was 0.70 g.

I.R.
$\nu_{max}^{Nujol}$ cm$^{-1}$ : 1775, 1700, 1680
N.M.R.
δ(Dimethylsulfoxide-d$_6$)ppm:
9.65 (1H, d)
8.95 (1H, s)
6.52 (1H, s)
5.7 (1H, d, d, J=5Hz, 9Hz)
5.16 (1H, d, J=5Hz)
3.97 (2H, ABq, J=13Hz)
3.72 (2H, ABq, J=18Hz)

What we claim is:

1. Compounds of the general formula:

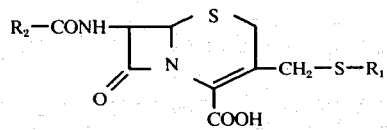

wherein
$R_1$ is a triazolyl, tetrazolyl or thiadiazolyl group, which may be substituted with lower alkyl group, and
$R_2$ is dichloro(lower)alkyl group, and their nontoxic, pharmaceutically acceptable salts.

2. Compounds according to claim 1, wherein $R_2$ is dichloromethyl group.

3. Compounds according to claim 2, wherein $R_1$ is triazolyl which may be substituted with lower alkyl group.

4. A compound according to claim 3, wherein $R_1$ is 4H-1,2,4-triazol-3-yl.

5. A compound according to claim 3, wherein $R_1$ is 1H-1,2,3-triazol-5-yl.

6. Compounds according to claim 2, wherein $R_1$ is tetrazolyl which may be substituted with lower alkyl group.

7. A compound according to claim 6, wherein $R_1$ is 1-methyl-1H-tetrazol-5-yl.

8. Compounds according to claim 2, wherein $R_1$ is thiadiazolyl which may be substituted with lower alkyl group.

9. A compound according to claim 8, wherein $R_1$ is 1,3,4-thiadiazol-2-yl.

10. A compound according to claim 8, wherein $R_1$ is 5-methyl-1,3,4-thiadiazol-2-yl.

* * * * *